(12) United States Patent
Petisce

(10) Patent No.: US 11,802,211 B2
(45) Date of Patent: Oct. 31, 2023

(54) POLYMERIC DYES AND USES THEREOF

(71) Applicant: Becton, Dickinson and Company, Franklin Lakes, NJ (US)

(72) Inventor: James R. Petisce, Westford, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 356 days.

(21) Appl. No.: 17/052,767

(22) PCT Filed: May 3, 2019

(86) PCT No.: PCT/US2019/030647
§ 371 (c)(1),
(2) Date: Nov. 3, 2020

(87) PCT Pub. No.: WO2019/213553
PCT Pub. Date: Nov. 7, 2019

(65) Prior Publication Data
US 2021/0230428 A1    Jul. 29, 2021

Related U.S. Application Data

(60) Provisional application No. 62/667,353, filed on May 4, 2018.

(51) Int. Cl.
*C09B 69/10* (2006.01)
*C08K 5/00* (2006.01)
*C08K 5/18* (2006.01)
*G01N 21/78* (2006.01)
*C12Q 1/04* (2006.01)
(Continued)

(52) U.S. Cl.
CPC .......... *C09B 69/109* (2013.01); *C08K 5/0041* (2013.01); *C08K 5/18* (2013.01); *C09B 69/103* (2013.01); *C12Q 1/045* (2013.01); *G01N 21/78* (2013.01); *G01N 2021/6439* (2013.01); *G01N 2021/773* (2013.01); *G01N 2021/7786* (2013.01)

(58) Field of Classification Search
CPC ... C09B 69/103; C09B 69/109; C08K 5/0041; C08K 5/18; G01N 21/78; G01N 2021/773; C12Q 1/045
See application file for complete search history.

(56) References Cited

U.S. PATENT DOCUMENTS 3,157,633 A    11/1964    Kuhn
3,886,865 A    6/1975    Ohto et al.
5,074,643 A    12/1991    Petisce
(Continued)

OTHER PUBLICATIONS

Makoto Obata, Mako Morita, Kayoko Nakase, Shigenobu Yano, Synthesis and Photophysical Properties of Rhodamine B Dye-Bearing Poly(isobutyl methacrylate-co-2,2, 2-trifluoroethyl methacrylate) as a Temperature-Sensing, Journal of Polymer Science: Part A: Polymer Chemistry, vol. 45, 2876-2885. (Year: 2007).*
(Continued)

*Primary Examiner* — Bijan Ahvazi
(74) *Attorney, Agent, or Firm* — Knobbe, Martens, Olson & Bear LLP

(57) ABSTRACT

Disclosed herein are polymeric dyes, their preparation, and their uses. Some embodiments relate to their use for detecting biological activity in samples, such as the presence of bacteria in blood.

21 Claims, 2 Drawing Sheets

(51) Int. Cl.
  *G01N 21/64* (2006.01)
  *G01N 21/77* (2006.01)

(56) References Cited

U.S. PATENT DOCUMENTS

| | | | |
|---|---|---|---|
| 5,266,486 A | 11/1993 | Fraatz et al. | |
| 7,976,585 B2* | 7/2011 | Cremer | C09B 69/101 |
| | | | 8/405 |
| 2013/0150571 A1* | 6/2013 | Banning | C07F 7/0838 |
| | | | 556/419 |
| 2014/0323703 A1 | 10/2014 | Cook et al. | |
| 2016/0251516 A1* | 9/2016 | Sorensen | G01N 21/80 |
| | | | 435/29 |
| 2018/0030210 A1* | 2/2018 | Leistner | C08G 77/392 |

OTHER PUBLICATIONS

Greene et al., [Eds.]—*Protecting Groups in Organic Synthesis*—(3rd Ed.) Wiley, New York (1999); TOC.
McOmie J.F.W. [Ed.]—*Protective Groups in Organic Chemistry*—Plenum Press, London & New York (1973); TOC.
Paquette L.A. [Ed.]—*Encyclopedia of Reagents for Organic Synthesis*—John Wiley & Sons (1995); TOC.
International Search Report and Written Opinion dated Aug. 27, 2019 for Application No. PCT/US2019/030647, filed May 3, 2019.
Extended European Search Report dated Mar. 16, 2022 for Application No. EP 19796518.9 in 9 pages.

* cited by examiner

POLYMERIC DYES AND USES THEREOF

INCORPORATION BY REFERENCE TO ANY PRIORITY APPLICATIONS

This application claims the benefit of U.S. Provisional Application No. 62/667,353, entitled Polymeric Dyes and Uses Thereof, filed May 4, 2018, the disclosure of which is incorporated herein by reference in its entirety.

BACKGROUND

Field

The present disclosure relates to the fields of chemistry and materials. More specifically, the present disclosure relates to polymeric dyes, their preparation, and their uses.

Description of the Related Art

In fields such as medicine, pharmaceuticals, and the food industry, one often needs to determine quickly and accurately whether bacteria or another microorganism has contaminated a particular system (e.g., a patient's blood, a batch of drug product, a lot of ice cream). Methods employing particles of fluorescent molecules embedded in polymeric matrices have been developed that indirectly detect microorganisms through their biological activities. See, for example, U.S. Pat. No. 5,266,486, which is hereby incorporated herein by reference in its entirety. However, such systems can suffer from uneven fluorophore distribution within the polymeric matrices because of phase separation and/or differential particle settling rates during the manufacturing, resulting in performance variability among sensors.

Thus, there is a need for improved fluorescent materials and methods for detecting biological activity within systems of interest.

SUMMARY

Some embodiments of the invention described herein relate to polymeric dyes comprising one or more fluorophores; and a polysiloxane composed of monomers A and B, optionally of monomer D, and two termini selected from the group consisting of —OR$^4$ and R$^4$, wherein A, B, D, and R$^4$ have any of the values described herein.

In some embodiments, A has the structure —Si(R$^1$)(R$^2$)O—, B has the structure —Si(R$^3$)(L)O—, and D if included has the structure —Si(R$^{15}$)(R$^{16}$)O—.

In some embodiments, R$^1$, R$^2$, R$^3$, and R$^{15}$ are each independently selected from the group consisting of C$_{1-6}$ alkyl and C$_{6-10}$ aryl.

L in some embodiments is a linker selected from the group consisting of —(CH$_2$)$_m$NHC(=O)—, —(CH$_2$)$_m$NHC(=O)NH—, —(CH$_2$)$_m$NHC(=S)NH—, —(CH$_2$)$_m$NHS(O$_2$)—, —(CH$_2$)$_m$NHC(=O)O—, —(CH$_2$)$_m$OC(=O)—, —(CH$_2$)$_m$NHC(=O)(CH$_2$)$_n$NHC(=O)—, —(CH$_2$)$_m$NHC(=O)(CH$_2$)$_n$NHC(=O)NH—, —(CH$_2$)$_m$NHC(=O)(CH$_2$)$_n$NHC(=S)NH—, —(CH$_2$)$_m$NHC(=O)(CH$_2$)$_n$NHS(O$_2$)—, —(CH$_2$)$_m$NHC(=O)(CH$_2$)$_n$NHC(=O)O—, —(CH$_2$)$_m$NHC(=O)(CH$_2$)$_n$C(=O)O—, —(CH$_2$)$_m$C(=O)NH(CH$_2$)$_n$NHC(=O)—, —(CH$_2$)$_m$C(=O)NH(CH$_2$)$_n$NHC(=O)NH—, —(CH$_2$)$_m$C(=O)NH(CH$_2$)$_n$NHC(=S)NH—, —(CH$_2$)$_m$C(=O)NH(CH$_2$)$_n$NHS(O$_2$)—, —(CH$_2$)$_m$C(=O)NH(CH$_2$)$_n$NHC(=O)O—, —(CH$_2$)$_m$C(=O)NH(CH$_2$)$_n$C(=O)O—, —(CH$_2$)$_m$OC(=O)(CH$_2$)$_n$NHC(=O)—, —(CH$_2$)$_m$OC(=O)(CH$_2$)$_n$NHC(=O)NH—, —(CH$_2$)$_m$OC(=O)(CH$_2$)$_n$NHC(=S)NH—, —(CH$_2$)$_m$OC(=O)(CH$_2$)$_n$NHS(O$_2$)—, —(CH$_2$)$_m$OC(=O)(CH$_2$)$_n$NHC(=O)O—, —(CH$_2$)$_m$OC(=O)(CH$_2$)$_n$C(=O)O—, —(CH$_2$)$_m$C(=O)O(CH$_2$)$_n$NHC(=O)—, —(CH$_2$)$_m$C(=O)O(CH$_2$)$_n$NHC(=O)NH—, —(CH$_2$)$_m$C(=O)O(CH$_2$)$_n$NHC(=S)NH—, —(CH$_2$)$_m$C(=O)O(CH$_2$)$_n$NHS(O$_2$)—, —(CH$_2$)$_m$C(=O)O(CH$_2$)$_n$NHC(=O)O—, —(CH$_2$)$_m$C(=O)O(CH$_2$)$_n$C(=O)O—, —(CH$_2$)$_m$NHC(=O)O(CH$_2$)$_n$NHC(=O)—, —(CH$_2$)$_m$NHC(=O)O(CH$_2$)$_n$NHC(=O)NH—, —(CH$_2$)$_m$NHC(=O)O(CH$_2$)$_n$NHC(=S)NH—, —(CH$_2$)$_m$NHC(=O)O(CH$_2$)$_n$NHS(O$_2$)—, —(CH$_2$)$_m$NHC(=O)O(CH$_2$)$_n$NHC(=O)O—, —(CH$_2$)$_m$NHC(=O)O(CH$_2$)$_n$C(=O)O—, —(CH$_2$)$_m$OC(=O)NH(CH$_2$)$_n$NHC(=O)—, —(CH$_2$)$_m$OC(=O)NH(CH$_2$)$_n$NHC(=O)NH—, —(CH$_2$)$_m$OC(=O)NH(CH$_2$)$_n$NHC(=S)NH—, —(CH$_2$)$_m$OC(=O)NH(CH$_2$)$_n$NHS(O$_2$)—, —(CH$_2$)$_m$OC(=O)NH(CH$_2$)$_n$NHC(=O)O—, —(CH$_2$)$_m$OC(=O)NH(CH$_2$)$_n$C(=O)O—, —(CH$_2$)$_m$S(CH$_2$)$_n$NHC(=O)—, —(CH$_2$)$_m$S(CH$_2$)$_n$NHC(=O)NH—, —(CH$_2$)$_m$S(CH$_2$)$_n$NHC(=S)NH—, —(CH$_2$)$_m$S(CH$_2$)$_n$NHS(O$_2$)—,

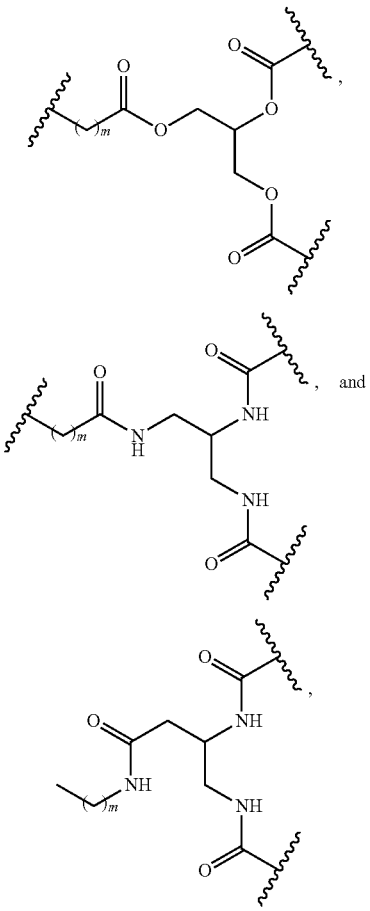

wherein m and n are each independently an integer from 1 to 5, and wherein L provides a covalent linkage to the one or more fluorophores.

In some embodiments, each R$^4$ is independently selected from the group consisting of H, —SH, halo, C$_{6-10}$ aryl, C$_{1-6}$ alkenyl,

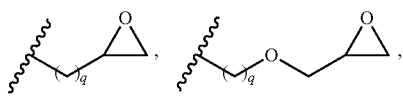

and $C_{1-6}$ alkyl optionally substituted with one or more $R^5$, —OC(═O)$R^6$, —N$R^7R^8$, —N$R^9$C(═O)$R^{10}$, and —N$R^{11}$C(═O)N$R^{12}R^{13}$, wherein q is an integer from 1 to 5.

In some embodiments, $R^5$ is —OH or —SH.

In some embodiments, $R^6$, $R^7$, $R^8$, $R^9$, $R^{10}$, $R^{11}$, $R^{12}$, and $R^{13}$ are each independently hydrogen or selected from the group consisting of $C_{1-6}$ alkyl, phenyl, and $C_{1-6}$ alkenyl, each optionally substituted with —OH, halo, —CN, $C_{1-6}$ alkoxy, and —NH$_2$.

In some embodiments, $R^{16}$ is

wherein s is an integer from 1 to 5.

Some embodiments herein relate to polymeric dyes comprising one or more rhodamine fluorophores; and covalently bonded to the one or more rhodamine fluorophores, a polymer selected from the group consisting of polysiloxane, polypropylene, poly(t-butyl methacrylate), fluorinated ethylene propylene, hexatriacontane, poly(tetrafluoroethylene), poly(hexafluoropropylene), and polyisobutylene, or a functionalized derivative thereof.

DETAILED DESCRIPTION

Polymeric Dyes and Embodiments Thereof

Figure 1:
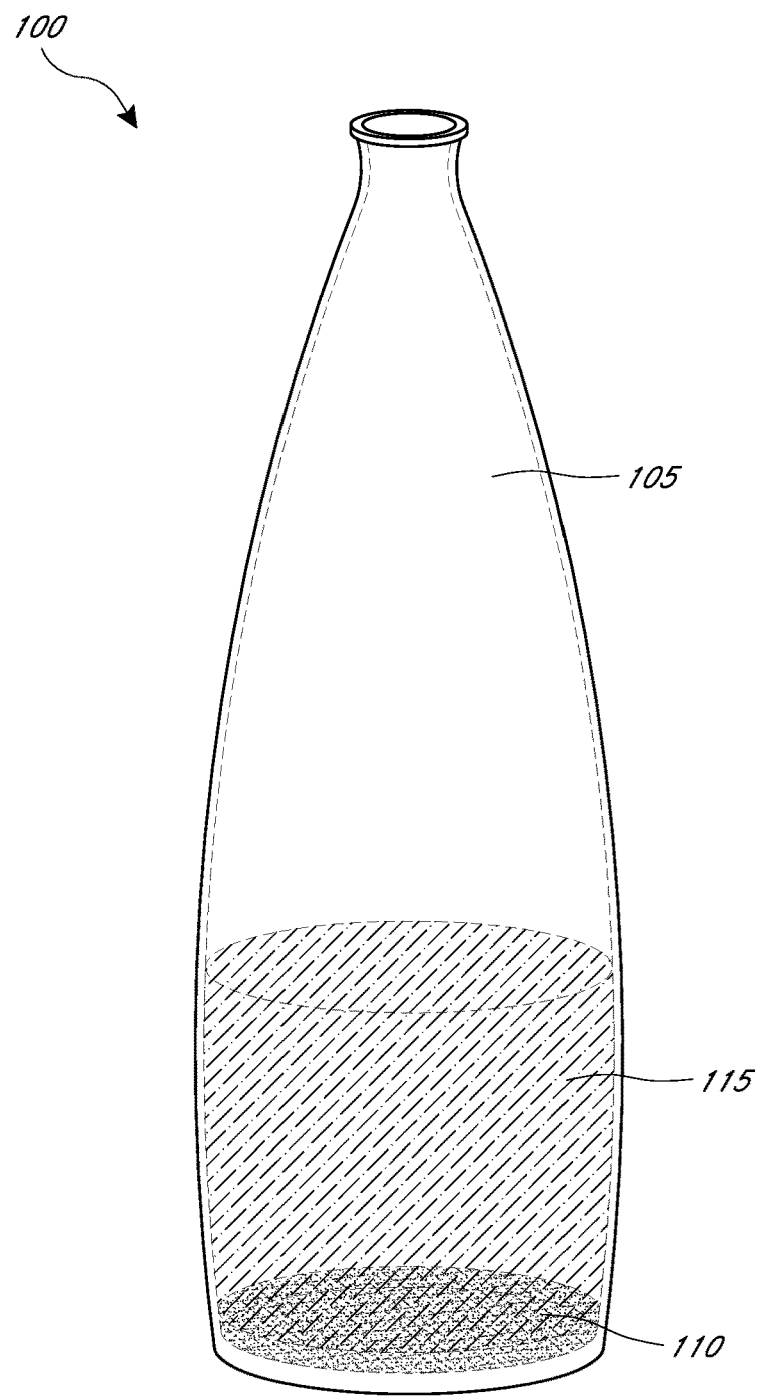
FIG. 1 illustrates an embodiment of vial sensor system 100, comprising a sealable, transparent container 105, a sensor polymer 110, and a biological culture medium 115.

In some embodiments of the present invention, fluorophores covalently attached to polymeric backbones are provided that, when used in microbial detection systems such as described in U.S. Pat. No. 5,266,486, which is incorporated herein by reference in its entirety, offer improved performance and manufacturability. Such polymeric dyes can replace the fluorophore particles used in the prior methods. Thus, the polymeric dyes can be combined with the polymer matrix in the sensor to produce an improved sensor. Polymeric dyes such as described herein can be entrapped in the non-fluorescent polymeric matrices by molecular entanglement and/or covalent-bond crosslinking to create the final sensor polymers. The specific polymeric backbone for the polymeric dye can be chosen to generally match the polarity of the non-fluorescent polymeric matrix. This match in polarity discourages phase separation and fluorophore aggregation during manufacturing. The entrapment of the polymeric dye and the matching in polarity, alone or in combination, completely avoid problems associated with differential settling time and afford sensor polymers lacking the manufacturing and performance problems associated with sensors created using prior methods.

The fluorophore can be any fluorescent molecule that is relatively inert under conditions used to grow a microorganism of interest. In some embodiments, the fluorophore is selected from one or more of a xanthene, a cyanine, a squaraine, a naphthalene, a coumarin, an oxadiazole, an anthracene, a pyrene, an oxazine, an acridine, an arylmethine, and a tetrapyrrole, or a derivative thereof. In some embodiments, the fluorophore is a xanthene or xanthene derivative. In some embodiments, the fluorophore is a xanthene derivative selected from Rhodamine 6G, Rhodamine 6G perchlorate, Rhodamine 19, Rhodamine B, Rhodamine 3B, Rhodamine 123, Rhodamine 110, Sulforhohdamine B, Sulforhodamine 101, Sulforhodamine G, Eosin B, Eosin Y, fluorescein, fluorescein-5-isothiocyanate, naphthofluorescein, carboxynaphthofluorescein, Pyronin B, and Oregon green.

In some embodiments of the polymeric dyes described above, the polymer covalently bonded to the fluorophore has a water contact angle of about 99 to 113 degrees when measured using ASTM Standard D7334-08, which is which is hereby incorporated herein by reference in its entirety. In some embodiments, the polymer covalently bonded to the fluorophore has a water contact angle of about 102 to 110 degrees when measured using ASTM Standard D7334-08. In some embodiments, the polymer covalently bonded to the fluorophore has a water contact angle of about 106 to 108 degrees when measured using ASTM Standard D7334-08.

In some embodiments of the polymeric dyes described above, the one or more fluorophores are rhodamine fluorophores selected from the group consisting of

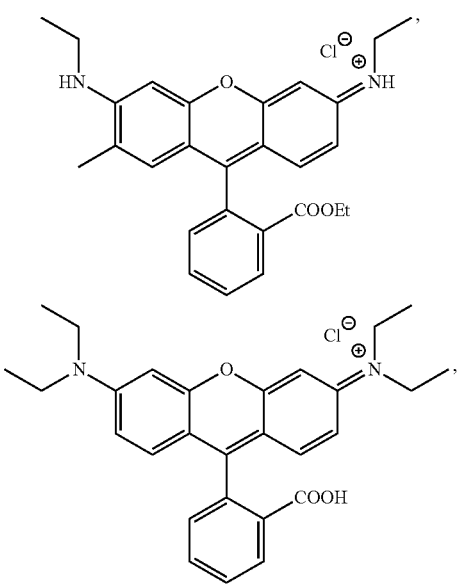

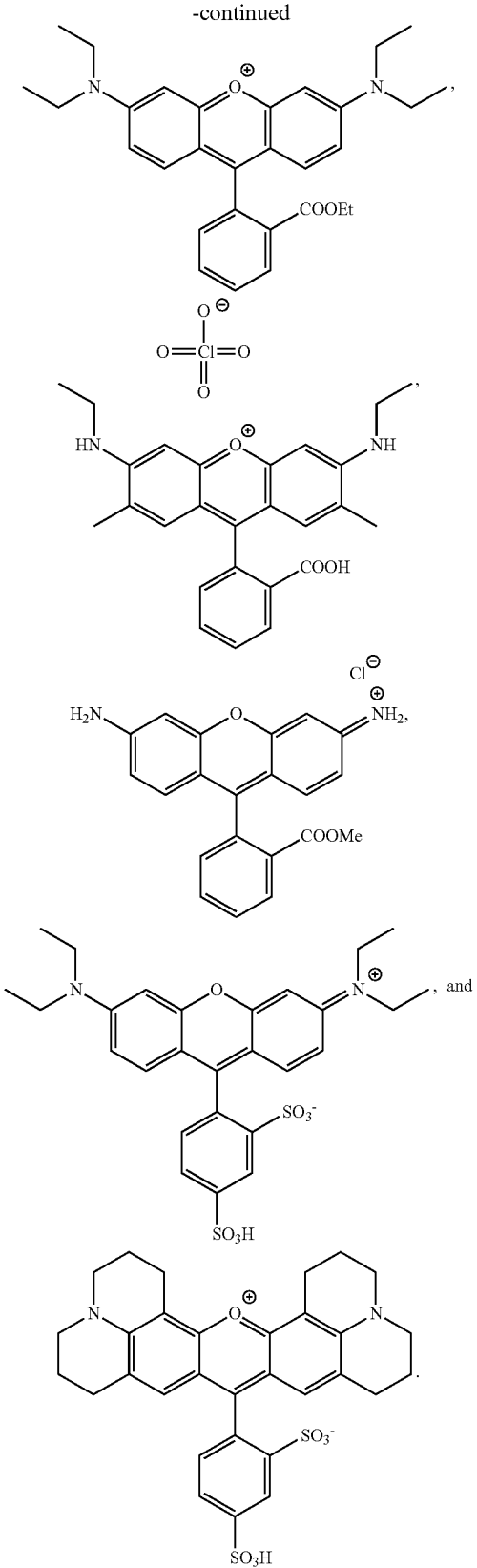

and two termini selected from the group consisting of —OR$^4$ and R$^4$, wherein A, B, D, and R$^4$ have any of the values described herein.

In some embodiments, A has the structure —Si(R$^1$)(R$^2$)O—, B has the structure —Si(R$^3$)(L)O—, and D if included has the structure —Si(R$^{15}$)(R$^{16}$)O—.

In some embodiments, R$^1$, R$^2$, R$^3$, and R$^{15}$ are each independently selected from the group consisting of C$_{1-6}$ alkyl and C$_{6-10}$ aryl.

L in some embodiments is a linker selected from the group consisting of —(CH$_2$)$_m$NHC(=O)—, —(CH$_2$)$_m$NHC(=O)NH—, —(CH$_2$)$_m$NHC(=S)NH—, —(CH$_2$)$_m$NHS(O$_2$)—, —(CH$_2$)$_m$NHC(=O)O—, —(CH$_2$)$_m$OC(=O)—, —(CH$_2$)$_m$NHC(=O)(CH$_2$)$_n$NHC(=O)—, —(CH$_2$)$_m$NHC(=O)(CH$_2$)$_n$NHC(=O)NH—, —(CH$_2$)$_m$NHC(=O)(CH$_2$)$_n$NHC(=S)NH—, —(CH$_2$)$_m$NHC(=O)(CH$_2$)$_n$NHS(O$_2$)—, —(CH$_2$)$_m$NHC(=O)(CH$_2$)$_n$NHC(=O)O—, —(CH$_2$)$_m$NHC(=O)(CH$_2$)$_n$C(=O)O— —(CH$_2$)$_m$C(=O)NH(CH$_2$)$_n$NHC(=O)—, —(CH$_2$)$_m$C(=O)NH(CH$_2$)$_n$NHC(=O)NH—, —(CH$_2$)$_m$C(=O)NH(CH$_2$)$_n$NHC(=S)NH—, —(CH$_2$)$_m$C(=O)NH(CH$_2$)$_n$NHS(O$_2$)—, —(CH$_2$)$_m$C(=O)NH(CH$_2$)$_n$NHC(=O)O—, —(CH$_2$)$_m$C(=O)NH(CH$_2$)$_n$C(=O)O—, —(CH$_2$)$_m$OC(=O)(CH$_2$)$_n$NHC(=O)—, —(CH$_2$)$_m$OC(=O)(CH$_2$)$_n$NHC(=O)NH—, —(CH$_2$)$_m$OC(=O)(CH$_2$)$_n$NHC(=S)NH—, —(CH$_2$)$_m$OC(=O)(CH$_2$)$_n$NHS(O$_2$)—, —(CH$_2$)$_m$OC(=O)(CH$_2$)$_n$NHC(=O)O—, —(CH$_2$)$_m$OC(=O)(CH$_2$)$_n$C(=O)O—, —(CH$_2$)$_m$C(=O)O(CH$_2$)$_n$NHC(=O)—, —(CH$_2$)$_m$C(=O)O(CH$_2$)$_n$NHC(=O)NH—, —(CH$_2$)$_m$C(=O)O(CH$_2$)$_n$NHC(=S)NH—, —(CH$_2$)$_m$C(=O)O(CH$_2$)$_n$NHS(O$_2$)—, —(CH$_2$)$_m$C(=O)O(CH$_2$)$_n$NHC(=O)O—, —(CH$_2$)$_m$C(=O)O(CH$_2$)$_n$C(=O)O—, —(CH$_2$)$_m$NHC(=O)O(CH$_2$)$_n$NHC(=O)—, —(CH$_2$)$_m$NHC(=O)O(CH$_2$)$_n$NHC(=O)NH—, —(CH$_2$)$_m$NHC(=O)O(CH$_2$)$_n$NHC(=S)NH—, —(CH$_2$)$_m$NHC(=O)O(CH$_2$)$_n$NHS(O$_2$)—, —(CH$_2$)$_m$NHC(=O)O(CH$_2$)$_n$NHC(=O)O—, —(CH$_2$)$_m$NHC(=O)O(CH$_2$)$_n$C(=O)O—, —(CH$_2$)$_m$OC(=O)NH(CH$_2$)$_n$NHC(=O)—, —(CH$_2$)$_m$OC(=O)NH(CH$_2$)$_n$NHC(=O)NH—, —(CH$_2$)$_m$OC(=O)NH(CH$_2$)$_n$NHC(=S)NH—, —(CH$_2$)$_m$OC(=O)NH(CH$_2$)$_n$NHS(O$_2$)—, —(CH$_2$)$_m$OC(=O)NH(CH$_2$)$_n$NHC(=O)O—, —(CH$_2$)$_m$OC(=O)NH(CH$_2$)$_n$C(=O)O—, —(CH$_2$)$_m$S(CH$_2$)$_n$NHC(=O)—, —(CH$_2$)$_m$S(CH$_2$)$_n$NHC(=O)NH—, —(CH$_2$)$_m$S(CH$_2$)$_n$NHC(=S)NH—, —(CH$_2$)$_m$S(CH$_2$)$_n$NHS(O$_2$)—,

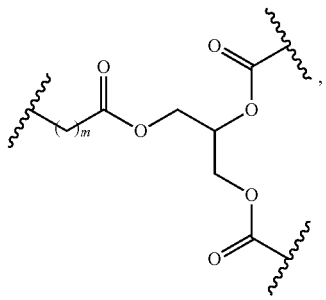

In some such embodiments, the polymer covalently bonded to the rhodamine fluorophore is a polysiloxane composed of monomers A and B, optionally of monomer D, -continued

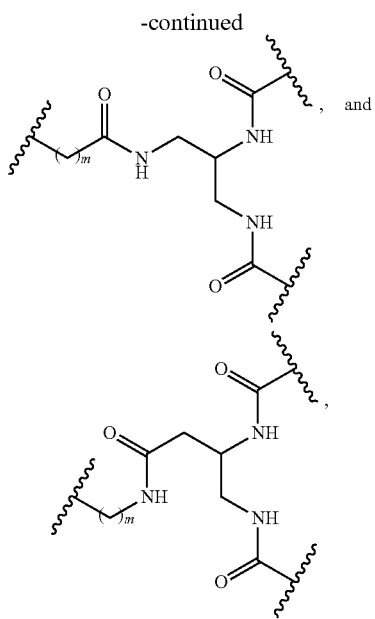

wherein m and n are each independently an integer from 1 to 5, and wherein L provides a covalent linkage to the one or more fluorophores. In some embodiments, m is 1. In some embodiments, m is 2. In some embodiments, m is 3. In some embodiments, m is 4. In some embodiments, m is 5. In some embodiments, n is 1. In some embodiments, n is 2. In some embodiments, n is 3. In some embodiments, n is 4. In some embodiments, n is 5.

With respect to the covalent linkage provided by L, L can link to the fluorophore through substitution at any position of the fluorophore that does not destroy the fluorescent capability of the fluorophore. In some embodiments containing rhodamine fluorophores, the position of substitution is at the 2' position of the carboxyphenyl or sulfophenyl ring in the fluorophore. In some embodiments containing rhodamine fluorophores, the position of substitution is at the 4' position of the carboxyphenyl or sulfophenyl ring. In some embodiments containing rhodamine fluorophores, the position of substitution is at the 5' position of the carboxyphenyl or sulfophenyl ring. In some embodiments containing rhodamine fluorophores, the position of substitution is at the 4' position of the carboxyphenyl or sulfophenyl ring on some monomers, and at the 5' position of the carboxyphenyl or sulfophenyl ring on other monomers.

Each $R^4$ in some embodiments is independently selected from the group consisting of H, —SH, halo, $C_{6-10}$ aryl, $C_{1-6}$ alkenyl,

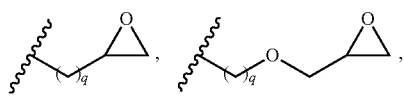

and $C_{1-6}$ alkyl optionally substituted with one or more $R^5$, —OC(=O)$R^6$, —$NR^7R^8$, —$NR^9C(=O)R^{10}$, and —$NR^{11}C(=O)NR^{12}R^{13}$, wherein q is an integer from 1 to 5.

$R^5$ in some embodiments is —OH or —SH.

In some embodiments, $R^6$, $R^7$, $R^8$, $R^9$, $R^{10}$, $R^{11}$, $R^{12}$, and $R^{13}$ are each independently hydrogen or selected from the group consisting of $C_{1-6}$ alkyl, phenyl, and $C_{1-6}$ alkenyl, each optionally substituted with —OH, halo, —CN, $C_{1-6}$ alkoxy, and —$NH_2$.

$R^1$ in some embodiments is $C_{1-6}$ alkyl. In some such embodiments, $R^1$ is methyl or ethyl. In some embodiments, $R^1$ is phenyl.

$R^2$ in some embodiments is $C_{1-6}$ alkyl. In some such embodiments, $R^2$ is methyl or ethyl. In some embodiments, $R^2$ is phenyl.

$R^3$ in some embodiments is $C_{1-6}$ alkyl. In some such embodiments, $R^3$ is methyl or ethyl. In some embodiments, $R^3$ is phenyl.

L in some embodiments is —$(CH_2)_m$NHC(=O)—, —$(CH_2)_m$NHC(=S)NH—, —$(CH_2)_m$NHC(=O)$(CH_2)_n$NHC(=O)—, —$(CH_2)_m$C(=O)NH$(CH_2)_n$NHC(=O)—, —$(CH_2)_m$NHC(=O)$(CH_2)_n$NHS($O_2$)—, —$(CH_2)_m$C(=O)NH$(CH_2)_n$NHS($O_2$)—,

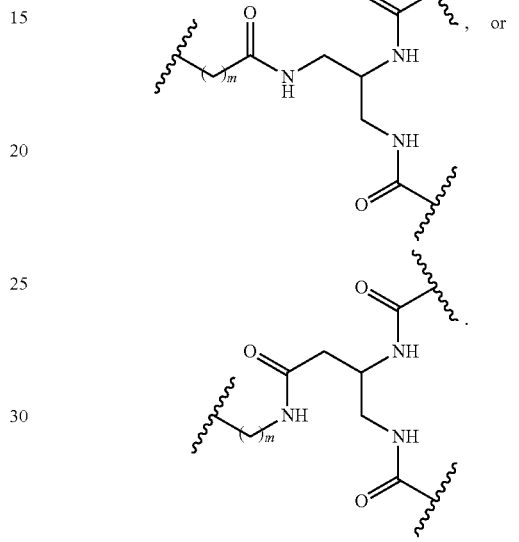

$R^4$ in some embodiments is H. In some embodiments, at least one $R^4$ is methyl, ethyl, or phenyl. In some embodiments, each $R^4$ is independently selected from the group consisting of methyl, ethyl, and phenyl. In some embodiments, each $R^4$ is independently selected from the group consisting of chloro and —OC(=O)$R^6$; wherein $R^6$ is $C_{1-6}$ alkyl or phenyl. In some embodiments, each $R^4$ is independently selected from the group consisting of —$NR^7R^8$, —$NR^9C(=O)R^{10}$, and —$NR^{11}C(=O)NR^{12}R^{13}$, and $R^7$, $R^8$, $R^9$, $R^{10}$, $R^{11}$, $R^{12}$, and $R^{13}$ are each independently selected from the group consisting of H and $C_{1-6}$ alkyl. In some embodiments, each $R^4$ is independently selected from the group consisting of H and vinyl. In some embodiments, each $R^4$ is independently $C_{1-6}$ alkyl substituted with one or more $R^5$; wherein $R^5$ is —OH. In some embodiments, each $R^4$ is independently $C_{1-6}$ alkyl substituted with one or more $R^5$; wherein $R^5$ is —SH. In some embodiments, $R^4$ is

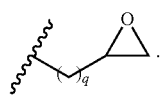

In some embodiments, $R^4$ is

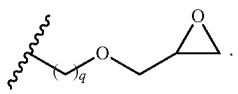

In some embodiments, q is 1. In some embodiments, q is 2. In some embodiments, q is 3. In some embodiments, q is 4. In some embodiments, q is 5.

In some embodiments, the polymeric dye contains monomer D having the structure —Si(R$^{15}$)(R$^{16}$)O—, wherein R$^{16}$ is

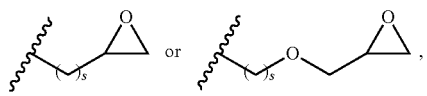

and wherein s is an integer from 1 to 5. In some particular embodiments, R$^{16}$ is

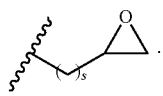

In some particular embodiments, R$^{16}$ is

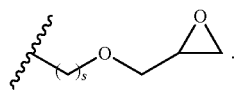

In some embodiments, s is 1. In some embodiments, s is 2. In some embodiments, s is 3. In some embodiments, s is 4. In some embodiments, s is 5.

In some embodiments, B is present in about 0.01 to 10 mol % in the polymeric dye. In some embodiments, B is present in about 0.5 to 5 mol % in the polymeric dye. In some embodiments, B is present in about 0.5 to 2.75 mol % in the polymeric dye. In some embodiments, B is present in about 2.75 to 5 mol % in the polymeric dye. In some embodiments, B is present in about 5 to 7.5 mol % in the polymeric dye. In some embodiments, B is present in about 7.5 to 10 mol % in the polymeric dye.

In some embodiments, the number average molar mass of the polymeric dye at least about 500 Dalton. In some embodiments, the number average molar mass of the polymeric dye is about 500 to 1500 Dalton. In some embodiments, the number average molar mass of the polymeric dye is about 1500 to 2500 Dalton. In some embodiments, the number average molar mass of the polymeric dye is about 2500 to 3500 Dalton. In some embodiments, the number average molar mass of the polymeric dye is about 3500 to 4500 Dalton. In some embodiments, the number average molar mass of the polymeric dye is about 4500 to 5500 Dalton. In some embodiments, the number average molar mass of the polymeric dye is about 5500 to 6500 Dalton. In some embodiments, the number average molar mass of the polymeric dye is about 6500 to 7500 Dalton. In some embodiments, the number average molar mass of the polymeric dye is about 7500 to 500 Dalton. In some embodiments, the number average molar mass of the polymeric dye is about 8500 to 9500 Dalton. In some embodiments, the number average molar mass of the polymeric dye is about 9500 to 10500 Dalton.

In some embodiments, the polysiloxane has the structure R$^4$O([Si(R$^1$)(R$^2$)—O—Si(R$^1$)(R$^2$)]$_x$—O—[Si(R$^1$)(R$^2$)—O—Si(R$^3$)(L)]$_y$)$_z$OR$^4$, wherein x, y, and z are each independently an integer. In some embodiments where the polysiloxane has the structure R$^4$O([Si(R$^1$)(R$^2$)—O—Si(R$^1$)(R$^2$)]$_x$—O—[Si(R$^1$)(R$^2$)—O—Si(R$^3$)(L)]$_y$)$_z$OR$^4$, x, y, and z are each independently an integer valued from 1-150. In some such embodiments, x, y, and z are each independently an integer valued from 3-75. In some such embodiments, x, y, and z are each independently an integer valued from 76-150. In some embodiments where the polysiloxane has the structure R$^4$O([Si(R$^1$)(R$^2$)—O—Si(R$^1$)(R$^2$)]$_x$—O—[Si(R$^1$)(R$^2$)—O—Si(R$^3$)(L)]$_y$)$_z$OR$^4$, R$^4$ at each terminus is C$_{1-6}$ alkyl. In some embodiments where the polysiloxane has the structure R$^4$O([Si(R$^1$)(R$^2$)—O—Si(R$^1$)(R$^2$)]$_x$—O—[Si(R$^1$)(R$^2$)—O—Si(R$^3$)(L)]$_y$)$_z$OR$^4$, R$^4$ at each terminus is H. In some embodiments where the polysiloxane has the structure R$^4$O([Si(R$^1$)(R$^2$)—O—Si(R$^1$)(R$^2$)]$_x$—O—[Si(R$^1$)(R$^2$)—O—Si(R$^3$)(L)]$_y$)$_z$OR$^4$, R$^4$ at one terminus is C$_{1-6}$ alkyl and R$^4$ at the second terminus is H. In some embodiments where the polysiloxane has the structure R$^4$O([Si(R$^1$)(R$^2$)—O—Si(R$^1$)(R$^2$)]$_x$—O—[Si(R$^1$)(R$^2$)—O—Si(R$^3$)(L)]$_y$)$_z$OR$^4$, the number average molar mass of the polymeric dye at least about 500 Dalton.

Some embodiments of the present invention include sensor polymers for detecting biological activity, comprising a polymeric dye as described herein and a non-fluorescent polymeric matrix. In some embodiments, the polymeric matrix is polysiloxane.

In some embodiments, the polymeric dye is entrapped within the polymeric matrix by molecular entanglement. Generally, molecular entanglement is accomplished by optimizing the molecular weight of the polymeric dye to the crosslinking density of the non-fluorescent polymeric matrix. Thus, in sensor polymer embodiments comprising non-fluorescent polymeric matrices with high crosslinking densities, lower molecular weight polymeric dyes can be used and still afford a sufficient degree of molecular entanglement. However, in sensor polymer embodiments comprising non-fluorescent polymeric matrices with lower crosslinking densities, higher molecular weight polymeric dyes generally will be needed to yield adequate entanglement. Skilled artisans can readily estimate the required molecular weight for the polymeric dye using known mathematical models and/or experimentation.

In some embodiments, the polymeric dye is covalently bonded to the polymeric matrix by crosslinking. Crosslinking can be accomplished by choosing a polymeric dye R$^4$ (e.g., 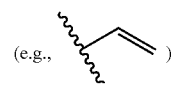 )

capable of conjugation with a moiety of the polymeric matrix (e.g., Si—H), and then reacting the functional group with the moiety using known chemical methods (e.g., platinum chemistry). Crosslinking can also be accomplished by inclusion of an appropriate quantity of the optional monomer D (e.g., 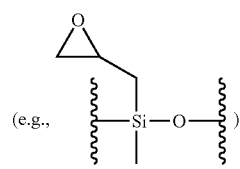 [SMILES: *O[Si](*)(C)CC1CO1] )

in the polymeric dye, and then conjugating a functional group on that monomer with a moiety of the polymeric matrix (e.g., 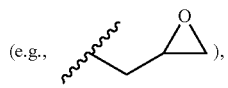), again using known chemical methods (e.g., addition of polyfunctional primary amines or catalytic homopolymerization).

The polymeric dye may be supplied as a liquid, a solid, or a solution of the polymeric dye in an appropriate solvent. If the polymeric dye is a solid or a viscous liquid, the polymeric dye can simply be blended into polymeric matrix to form the sensor polymer. Alternatively, a solid or viscous liquid polymeric dye may be dissolved in an appropriate solvent, mixed with the polymeric matrix, which itself might be dissolved in an appropriate solvent, and then the solvent(s) evaporated to yield the sensor polymer. If the polymeric dye is supplied as a solution, then the solution may be mixed with the polymeric matrix, which itself might be dissolved in an appropriate solvent, and then the solvent(s) can be evaporated to yield the sensor polymer. Alternatively, the solvent of the polymeric dye solution may be removed, and then the polymeric dye mixed directly with the polymeric matrix.

Some embodiments of the present invention include vial sensor systems for detecting biological activity in a sample, such vial sensor systems comprising: a sealable, transparent container having an inner surface; a sensor polymer, as described herein, attached to at least a portion of the inner surface of the container; and a biological culture medium within the container. FIG. 1 illustrates an example of a vial sensor system 100, where the transparent container, sensor polymer, and biological culture medium are indicated by 105, 110, and 115, respectively. In some embodiments, the vial sensor system can be used to detect microbial activity in a sample, such as a blood sample.

The biological culture medium can be any culture medium known to those skilled in the art as appropriate for sustaining growth of microorganisms of interest. In some embodiments, the biological culture medium comprises enriched soybean-casein digest broth. In some embodiments, the biological culture medium comprises tryptic soy broth. In some embodiments, the biological culture medium comprises lysogeny broth. In some embodiments, the biological culture medium comprises chopped meat medium. In some embodiments, the biological culture medium comprises modified chopped meat medium. In some embodiments, the biological culture medium comprises brain heart infusion broth. In some embodiments, the biological culture medium comprises maltose broth. In some embodiments, the biological culture medium comprises modified maltose broth. In some embodiments, the biological culture medium comprises *Mitis salivarius* broth. In some embodiments, the biological culture medium comprises MacConkey broth. In some embodiments, the biological culture medium further comprises an agent that neutralizes antibiotics. In some such embodiments, the agent that neutralizes antibiotics is a cationic exchange resin. In some such embodiments, the agent that neutralizes antibiotics is a hydrophobic resin. In some embodiments, the biological culture medium further comprises an agent that lyses blood cells.

In some embodiments of the vial sensor systems, one type of sensor polymer is attached to at least a portion of the inner surface of the container. In some embodiments, a more than one type of sensor polymer are attached to at least a portion of the inner surface of the container. In some embodiments, two types of sensor polymer are attached to at least a portion of the inner surface of the container. In some embodiments, three types of sensor polymer are attached to at least a portion of the inner surface of the container.

Some embodiments of the vial sensor systems additionally comprise an indicator within the container. The indicator of the vial sensor systems can be any substance that modulates excitation and/or emission of the fluorescent signal from the fluorophore. In some embodiments, the indicator is selected from the group consisting of propyl red, p-nitrophenol, azolitmin, bromocresol purple, chlorophenol red, 3,6-dihydroxy xanthone, alizarin, brom xylenol blue, aurin, phenol red, Cleve's acid, orcinaurine, neutral red, and lead acetate. In some embodiments, the indicator is capable of undergoing a light absorbance change in response to a pH change. In some embodiments, the indicator is selected from the group consisting of propyl red, p-nitrophenol, azolitmin, chlorophenyl red, 3,6-dihydroxy xanthone, alizarin, bromxylenol blue, m-dinitrobenzoyleneurea, bromthymol blue, aurin (aosolic acid), neutral red, cresol red, bromocresol purple, resolic acid, nile blue, phenol red, nitramine, cresol purple, and methyl yellow. In some embodiments, the indicator modulates excitation and/or emission of the fluorescent signal from the fluorophore in response to a change in concentration of at least one substance selected from the group consisting of $CO_2$, $H_2CO_3$, $H^+$, $H_3O^+$, $NH_3$, $NH_4^+$, $H_2S$, $H_2$, and metal ions. In some embodiments, the indicator modulates excitation and/or emission of the fluorescent signal from the fluorophore in response to a change in concentration of $H_2CO_3$, $H^+$, and/or $H_3O^+$.

Figure 2:
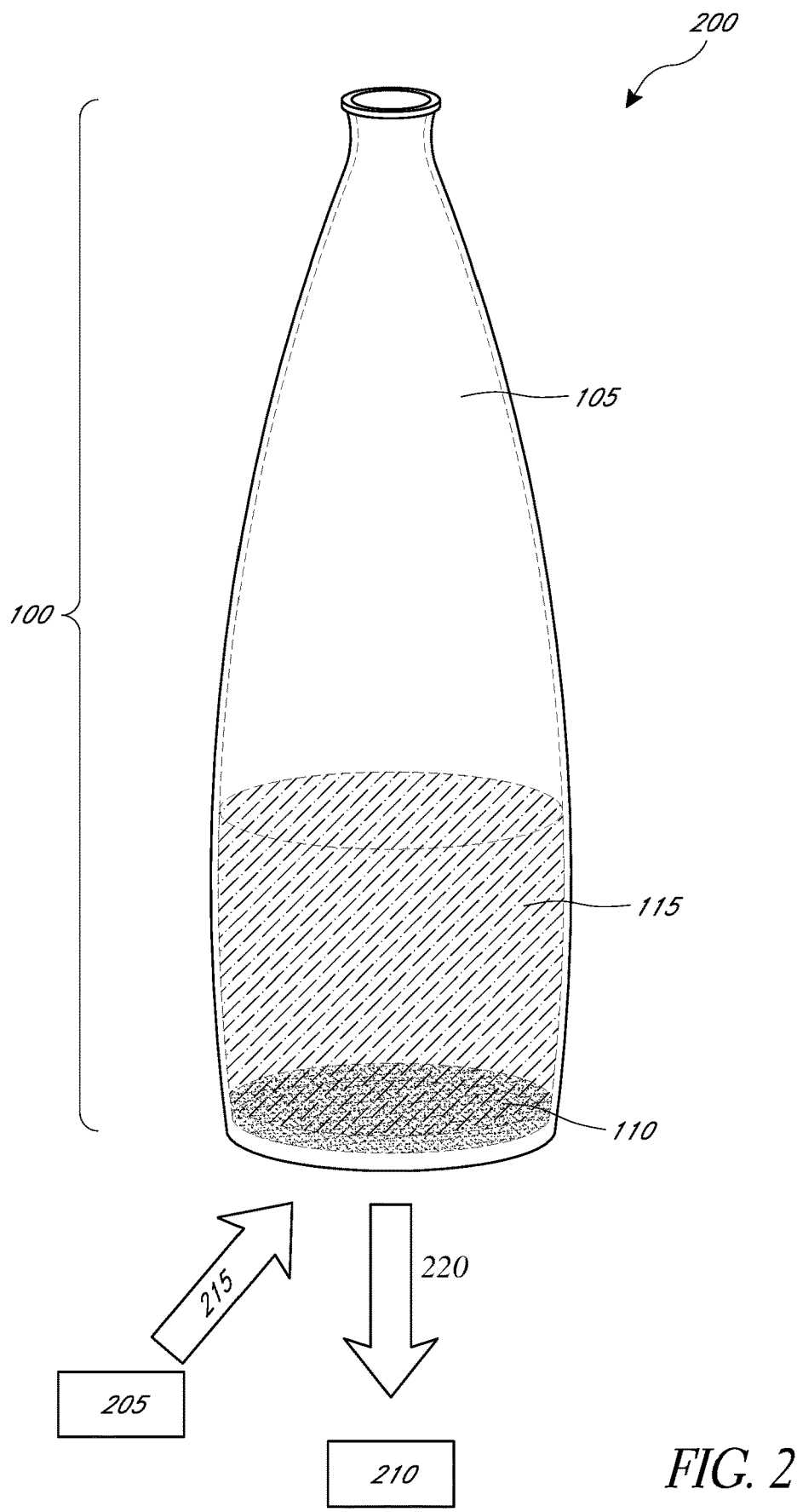
FIG. 2 illustrates an embodiment of apparatus 200 for detecting biological activity in a sample. Apparatus 200 comprises a vial sensor system 100 as depicted in FIG. 1, and additionally comprises a light source 205 external to the vial sensor system and a detector 210 for detecting fluorescent radiation. Arrows 215 and 220 indicate light emitted from the light source and light approaching the detector, respectively.

Some embodiments of the present invention include an apparatus for detecting biological activity in a sample. In some embodiments, such an apparatus comprises a vial sensor system as described herein; a light source external to the sensor; and a detector for detecting fluorescent radiation. FIG. 2 illustrates an example of apparatus 200 for detecting biological activity in a sample. As disclosed above, the vial sensor system 100 comprises a target container 105, a sensor polymer 110, and a biological culture medium 115. Apparatus 200 additionally comprises a light source 205 external to the sensor and a detector 210 for detecting fluorescent radiation.

The light source can be any source that provides light at the excitation wavelengths of the fluorophore. In some embodiments, the light source is a mercury-arc lamp. In some embodiments, the light source is a tungsten-halogen lamp. In some embodiments, the light source is a laser. In some embodiments, the light source is light-emitting diode. In some embodiments, the apparatus for detecting biological activity also comprises an excitation filter between the light source 205 and vial sensor system 100 such that the light 215 reaching the vial sensor system is substantially only of wavelengths appropriate for fluorophore excitation.

The detector can be any device that will provide an electric signal proportional to or correlatable with light intensity. In some embodiments, the detector is a photodiode. In some embodiments, the detector is a silicon photodiode. In some embodiments, the detector is a PIN silicon diode. In some embodiments, the detector is a GaAsP photodiode. In some embodiments, the detector is a photoresistor. In some embodiments, the detector is a photovoltaic. In some embodiments, the detector is a photoconductor. In some embodiments, the apparatus for detecting biological activity also comprises an emission filter between the vial sensor system 100 and detector 210 such that the light 220 reaching the detector is substantially only of wavelengths emitted by the relaxing fluorophore.

Some embodiments of the present invention include methods of making a polymeric dye, comprising: obtaining a polysiloxane composed of monomers A and C, and optionally of monomer D, wherein A has the structure —Si($R^1$)($R^2$)O—, C has the structure —Si($R^{14}$)(M)O—, and D if included has the structure —Si($R^{15}$)($R^{16}$)O—, wherein $R^1$, $R^2$, $R^{14}$, and $R^{15}$ are each independently selected from the group consisting of $C_{1-6}$ alkyl and $C_{6-10}$ aryl, wherein moiety M is selected from the group consisting of —$(CH_2)_o NH_2$, —$(CH_2)_o SH$, and —$(CH_2)_o NHC(=O)(CH_2)_p NH_2$, wherein o and p are each independently an integer from 1 to 5, wherein $R^{16}$ is

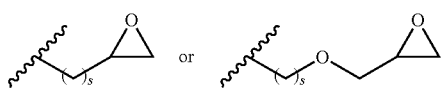

wherein s is an integer from 1 to 5, wherein B is present in about 0.5 to 5.0 mol % in the polymer, and wherein the number average molar mass of the polysiloxane is about 1000 to 3000 Dalton; obtaining a rhodamine fluorophore; and reacting the polysiloxane with the rhodamine fluorophore to form a covalent bond between the polysiloxane and the rhodamine fluorophore.

In some embodiments, the method of making a polymeric dye further comprises functionalizing one or both terminal —OH by substitution with $R^4$, wherein $R^4$ is selected from the group consisting of H, —SH, halo, $C_{6-10}$ aryl, $C_{1-6}$ alkenyl, $C_{1-6}$ alkyl optionally substituted with one or more $R^5$, —OC(=O)$R^6$, —$NR^7R^8$, —$NR^9C(=O)R^{10}$, —$NR^{11}C(=O)NR^{12}R^{13}$,

wherein q is an integer from 1 to 5; wherein $R^5$ is —OH or —SH; and wherein $R^6$, $R^7$, $R^8$, $R^9$, $R^{10}$, $R^{11}$, $R^{12}$, and $R^{13}$ are each independently hydrogen or selected from the group consisting of $C_{1-6}$ alkyl, phenyl, and $C_{1-6}$ alkenyl, each optionally substituted with —OH, halo, —CN, $C_{1-6}$ alkoxy, and —$NH_2$.

Some embodiments of the present invention include methods of making a sensor polymer for detecting biological activity, comprising: obtaining a polymeric dye as described herein; obtaining siloxane monomer; dissolving the polymeric dye and siloxane monomer to form a polymerization solution; and subjecting the polymerization solution to appropriate conditions to form a polymeric dye entrapped within or covalently bonded to a polysiloxane.

Some embodiments of the present invention include methods of detecting biological activity in a sample, the method comprising: placing the sample or a portion of the sample in a culture medium, to form a sample-culture medium, said sample-culture medium capable of sustaining growth of microorganisms; incubating the sample-culture medium in the container of a vial sensor system at conditions capable of sustaining growth of the microorganisms; exposing the vial sensor system to a light source; and detecting fluorescent light emitted from the vial sensor system to create fluorescent light data, wherein the fluorescent light data is indicative of biological activity.

Methods of Preparation

The polymeric dyes described herein can be prepared using synthetic techniques generally known to those skilled in the art. For example, hydrolyzing appropriate dichlorosilanes or diacetoxysilanes in desired molar proportions can afford a polysiloxane backbone, which can then be coupled to a fluorophore such as 5-carboxy Rhodamine 6G (Toronto Research Chemicals, Catalogue No. C181700) using uronium-type reagents or carbodiimide reagents, to produce a polymeric dye as described herein with two Si—OH termini. The number average molecular weight of the polymeric dye can be controlled at the hydrolysis step by employing appropriate reaction conditions (temperature, concentration, etc.) or by introducing an appropriate quantity of a polymerization-terminating monomer such as chlorotrimethylsilane or chlorotriphenylsilane. Alternatively, it may be desirable to attach the fluorophore before polymerization, i.e. synthesize fluorophore-dichlorosilanes or fluorophore-diacetoxysilanes for polymerization. In some circumstances, the use of a conventional protecting group may be necessary to protect sensitive portions of the fluorophore or the functional group on monomer B/C to be coupled to the fluorophore.

Backbones for the fluorophore other than polysiloxane also can be prepared using synthetic techniques generally known to those skilled in the art. For example, poly(t-butyl methacrylate) can be prepared from t-butyl methacrylate through solution, emulsion, or bulk polymerization using a free radical initiator such as azobisisobutyronitrile. The number average molecular weight of these reactions can be controlled by the choice of polymerization technique (i.e., solution, emulsion, or bulk polymerization), temperature, and/or by the amount of free radical initiator, for example. Functionalization for coupling to the fluorophore can be accomplished by partial hydrolysis of the t-butyl ester groups after polymerization, or by inclusion of a monomer such as hydroxyethylmethacrylate or 2-chloroethyl methacrylate during polymerization.

The polymeric backbone termini of the polymeric dyes can be functionalized for cross-linking by synthetic techniques generally known to those skilled in the art. For example, the hydroxyl termini of a polysiloxane backbone can be converted to a suitable leaving group, such as benzhydryloxy, and then reduced with lithium aluminum hydride to form the corresponding silyl hydride. The Si—OH termini could alternatively be converted to Si—Cl, and then reacted with an alkenyl lithium reagent or alkenyl Grignard reagent to yield alkene-functionalized termini.

Regarding the sensor polymer, the polymeric dye can be dissolved in the monomer solution of the non-fluorescent polymeric matrix. Once polymerized, the non-fluorescent polymeric matrix can entrap the polymeric dye via molecular entanglement if the polymeric dye possesses a number average molecular weights greater than about 500 Dalton. The polymeric dyes can also be covalently bonded to the non-fluorescent polymeric matrix by crosslinking reactions generally known to those skilled in the art. For example, polymeric dyes with polysiloxane backbones containing Si—H termini can be crosslinked with non-fluorescent polysiloxane matrices, using platinum catalysts such as Karstedt's catalyst, to form ethylene linkages. Alternatively, polymeric dyes with polysiloxane backbones containing alkene-functionalized termini can react with thiol groups on the non-fluorescent polymeric matrix, via free-radical or Michael addition pathways, to form alkyl sulfide crosslinks.

The compounds disclosed herein may be synthesized by methods described above, or by modification of these methods. Ways of modifying the methodology include, among others, temperature, solvent, reagents, etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include, e.g., those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:

Et Ethyl
Me Methyl
Tert, t tertiary

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or Cm aryl," or similar designations. Examples of aryl groups include, but are not limited to, phenyl, naphthyl, azulenyl, and anthracenyl.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

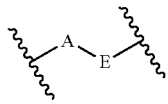

includes the substituent being oriented such that the A is attached at the leftmost attachment point of the molecule as well as the case in which A is attached at the rightmost attachment point of the molecule.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

What is claimed is:
1. A polymeric dye comprising:
one or more rhodamine fluorophores selected from the group consisting of

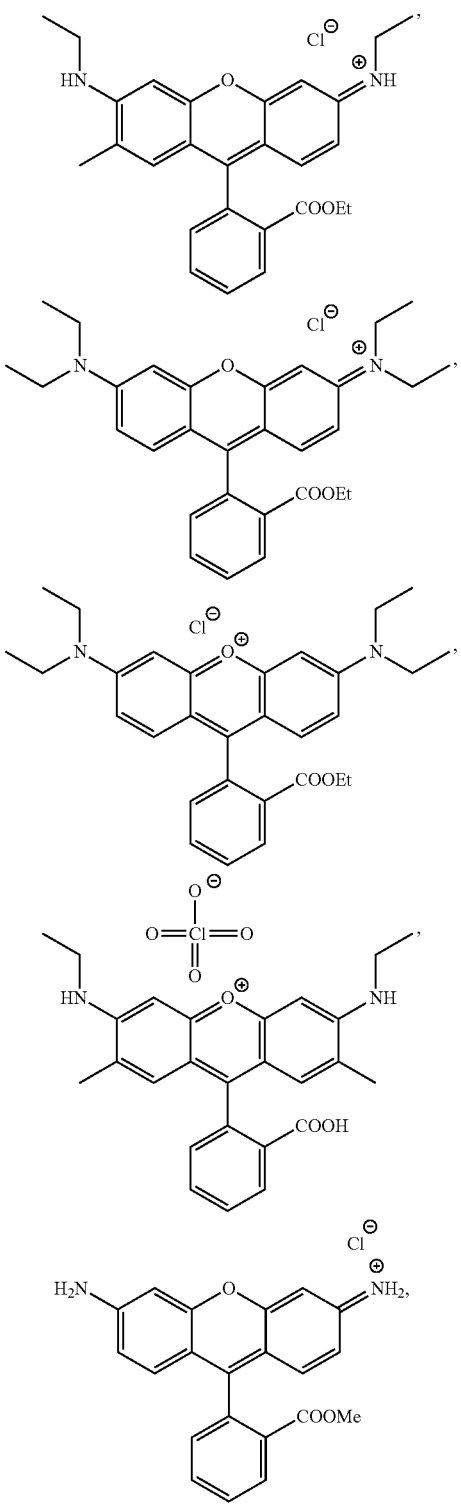

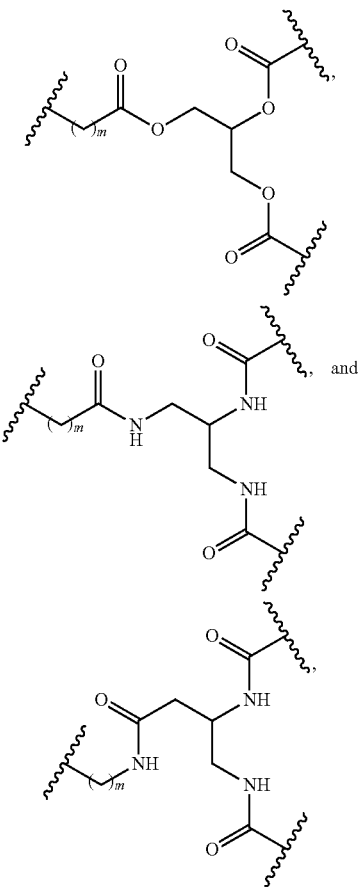

and
covalently bonded to the one or more rhodamine fluorophores, a polymer, wherein the polymer is a polysiloxane composed of monomers A and B, optionally of monomer D, and two termini selected from the group consisting of —$OR^4$ and $R^4$, wherein:

A has the structure —$Si(R^1)(R^2)O$—, B has the structure —$Si(R^3)(L)O$—, and D has the structure —$Si(R^{15})(R^{16})O$—;

$R^1$, $R^2$, $R^3$, and $R^{15}$ are each independently selected from the group consisting of $C_{1-6}$ alkyl and $C_{6-10}$ aryl;

L is a linker selected from the group consisting of —$(CH_2)_mNHC(=O)$—, —$(CH_2)_mNHC(=O)NH$—, —$(CH_2)_mNHC(=S)NH$—, —$(CH_2)_mNHS(O_2)$—, —$(CH_2)_mNHC(=O)O$—, —$(CH_2)_mOC(=O)$—, —$(CH_2)_mNHC(=O)(CH_2)_nNHC(=O)$—, —$(CH_2)_mNHC(=O)(CH_2)_nNHC(=O)NH$—, —$(CH_2)_mNHC(=O)(CH_2)_nNHC(=S)NH$—, —$(CH_2)_mNHC(=O)(CH_2)_nNHS(O_2)$—, —$(CH_2)_mNHC(=O)(CH_2)_nNHC(=O)O$—, —$(CH_2)_mNHC(=O)(CH_2)_nC(=O)O$—, —$(CH_2)_mC(=O)NH(CH_2)_nNHC(=O)$—, —$(CH_2)_mC(=O)NH(CH_2)_nNHC(=O)NH$—, —$(CH_2)_mC(=O)NH(CH_2)_nNHC(=S)NH$—, —$(CH_2)_mC(=O)NH(CH_2)_nNHS(O_2)$—, —$(CH_2)_mC(=O)NH(CH_2)_nNHC(=O)O$—, —$(CH_2)_mC(=O)NH(CH_2)_nC(=O)O$—, —$(CH_2)_mOC(=O)(CH_2)_nNHC(=O)$—, —$(CH_2)_mOC(=O)(CH_2)_nNHC(=O)NH$—, —$(CH_2)_mOC(=O)(CH_2)_nNHC(=S)NH$—, —$(CH_2)_mOC(=O)(CH_2)_nNHS(O_2)$—, —$(CH_2)_mOC(=O)(CH_2)_nNHC(=O)O$—, —$(CH_2)_mOC(=O)(CH_2)_nC(=O)O$—, —$(CH_2)_mC(=O)O(CH_2)_nNHC(=O)$—, —$(CH_2)_mC(=O)O(CH_2)_nNHC(=O)NH$—, —$(CH_2)_mC(=O)O(CH_2)_nNHC(=S)NH$—, —$(CH_2)_mC(=O)O(CH_2)_nNHS(O_2)$—, —$(CH_2)_mC(=O)O(CH_2)_nNHC(=O)O$—, —$(CH_2)_mC(=O)O(CH_2)_nC(=O)O$—, —$(CH_2)_mNHC(=O)O(CH_2)_nNHC(=O)$—, —$(CH_2)_mNHC(=O)O(CH_2)_nNHC(=O)NH$—, —$(CH_2)_mNHC(=O)O(CH_2)_nNHC(=S)NH$—, —$(CH_2)_mNHC(=O)O(CH_2)_nNHS(O_2)$—, —$(CH_2)_mNHC(=O)O(CH_2)_nNHC(=O)O$—, —$(CH_2)_mNHC(=O)O(CH_2)_nC(=O)O$—, —$(CH_2)_mOC(=O)NH$ $(CH_2)_nNHC(=O)$—, —$(CH_2)_mOC(=O)NH(CH_2)_nNHC(=O)NH$—, —$(CH_2)_mOC(=O)NH(CH_2)_nNHC(=S)NH$—, —$(CH_2)_mOC(=O)NH(CH_2)_nNHS(O_2)$—, —$(CH_2)_mOC(=O)NH(CH_2)_nNHC(=O)O$—, —$(CH_2)_mOC(=O)NH(CH_2)_nC(=O)O$—, —$(CH_2)_mS(CH_2)_nNHC(=O)$—, —$(CH_2)_mS(CH_2)_nNHC(=O)NH$—, —$(CH_2)_mS(CH_2)_nNHC(=S)NH$—, —$(CH_2)_mS(CH_2)_nNHS(O_2)$—,

wherein m and n are each independently an integer from 1 to 5, and wherein L provides a covalent linkage to the one or more fluorophores;

each $R^4$ is independently selected from the group consisting of H, —SH, halo, $C_{6-10}$ aryl, $C_{1-6}$ alkenyl, and $C_{1-6}$ alkyl optionally substituted with one or more $R^5$, —$OC(=O)R^6$, —$NR^7R^8$, —$NR^9C(=O)R^{10}$, and —$NR^{11}C(=O)NR^{12}R^{13}$, wherein q is an integer from 1 to 5;

$R^5$ is —OH or —SH;

$R^6$, $R^7$, $R^8$, $R^9$, $R^{10}$, $R^{11}$, $R^{12}$, and $R^{13}$ are each independently hydrogen or each independently selected from the group consisting of $C_{1-6}$ alkyl, phenyl, and $C_{1-6}$ alkenyl, each optionally substituted with —OH, halo, —CN, $C_{1-6}$ alkoxy, and —$NH_2$; and

21

$R^{16}$ is

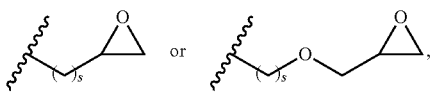

wherein s is an integer from 1 to 5.

2. The polymeric dye according to claim 1, wherein $R^1$, $R^2$, and $R^3$ are independently $C_{1-6}$ alkyl or phenyl.

3. The polymeric dye according to claim 1, wherein L is —$(CH_2)_m$NHC(=O)—, —$(CH_2)_m$NHC(=S)NH—, —$(CH_2)_m$NHC(=O)$(CH_2)_n$NHC(=O)—, —$(CH_2)_m$C(=O)NH$(CH_2)_n$NHC(=O)—, —$(CH_2)_m$NHC(=O)$(CH_2)_n$NHS$(O_2)$—, —$(CH_2)_m$C(=O)NH$(CH_2)_n$NHS$(O_2)$—,

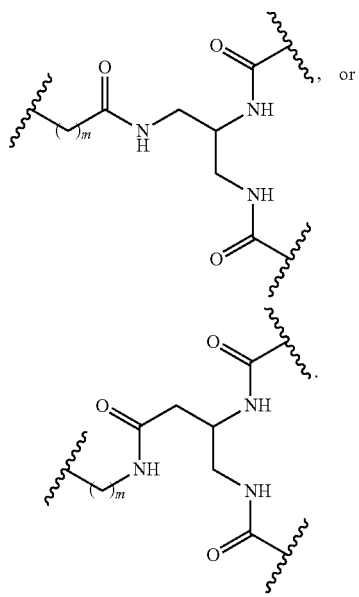

4. The polymeric dye according to claim 1, wherein each $R^4$ is H.

5. The polymeric dye according to claim 1, wherein at least one $R^4$ is methyl, ethyl, or phenyl.

6. The polymeric dye of according to claim 1, wherein each $R^4$ is independently selected from the group consisting of methyl, ethyl, and phenyl.

7. The polymeric dye according to claim 1, wherein each $R^4$ is independently selected from the group consisting of chloro, —OC(=O)$R^6$, —$NR^7R^8$, —$NR^9C(=O)R^{10}$, and —$NR^{11}C(=O)NR^{12}R^{13}$; wherein $R^6$ is $C_{1-6}$ alkyl or phenyl and wherein $R^7$, $R^8$, $R^9$, $R^{10}$, $R^{11}$, $R^{12}$, and $R^{13}$ are each independently selected from the group consisting of H and $C_{1-6}$ alkyl.

8. The polymeric dye according to claim 1, wherein each $R^4$ is independently selected from the group consisting of H and vinyl.

9. The polymeric dye of according to claim 1, wherein each $R^4$ is independently $C_{1-6}$ alkyl substituted with one or more $R^5$; wherein $R^5$ is —OH or —SH.

10. The polymeric dye according to claim 1, wherein the polymeric dye contains monomer D having the structure —Si$(R^{15})(R^{16})$O—.

22

11. The polymeric dye according to claim 10, wherein $R^{16}$ is

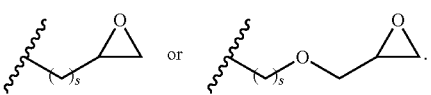

12. The polymeric dye according to claim 1, wherein B is present in about 0.5 to 5 mol % in the polymeric dye.

13. The polymeric dye according to claim 1, wherein the number average molar mass of the polymeric dye at least about 500 Dalton.

14. The polymeric dye according to claim 1, wherein the polysiloxane has the structure $R^4$O([Si$(R^1)(R^2)$—O—Si$(R^1)(R^2)]_x$—O—[Si$(R^1)(R^2)$—O—Si$(R^3)(L)]_y)_z$O$R^4$, and wherein x, y, and z are each independently an integer.

15. A sensor polymer for detecting biological activity, comprising:
the polymeric dye according to claim 1; and
a non-fluorescent polymeric matrix.

16. The sensor polymer according to claim 15, wherein the polymeric dye is entrapped within the polymeric matrix.

17. A vial sensor system for detecting biological activity in a sample, the vial sensor system comprising:
a sealable, transparent container having an inner surface;
the sensor polymer according to claim 15 attached to at least a portion of the inner surface of the container; and
a biological culture medium within the container.

18. The vial sensor system according to claim 17, additionally comprising an indicator within the container.

19. An apparatus for detecting biological activity in a sample, said apparatus comprising:
the vial sensor system of according to claim 17;
a light source external to the sensor; and
a detector for detecting fluorescent radiation.

20. A method of making a polymeric dye, comprising:
obtaining a polysiloxane composed of monomers A and C, and optionally of monomer D according to claim 1, wherein:
A has the structure —Si$(R^1)(R^2)$O—, C has the structure —Si$(R^{14})$(M)O—, and D has the structure —Si$(R^{15})(R^{16})$O—;
$R^1$, $R^2$, $R^{14}$, and $R^{15}$ are each independently selected from the group consisting of $C_{1-6}$ alkyl and $C_{6-10}$ aryl;
moiety M is selected from the group consisting of —$(CH_2)_o$NH$_2$, —$(CH_2)_o$SH, and —$(CH_2)_o$NHC(=O)$(CH_2)_p$NH$_2$, wherein o and p are each independently an integer from 1 to 5;
$R^{16}$ is

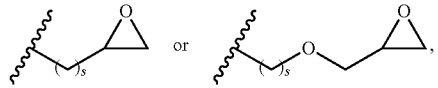

wherein s is an integer from 1 to 5;
B is present in about 0.5 to 5 mol %; and
the number average molar mass of the polysiloxane is about 1000 to 3000 Dalton;
obtaining a rhodamine fluorophore; and
reacting the polysiloxane with the rhodamine fluorophore to form a covalent bond between the polysiloxane and the rhodamine fluorophore.

21. A method of detecting biological activity in a sample, the method comprising:
- placing the sample or a portion of the sample in a culture medium, to form a sample-culture medium, said sample-culture medium capable of sustaining growth of microorganisms;
- incubating the sample-culture medium in the container of the vial sensor system of according to claim 17 at conditions capable of sustaining growth of the microorganisms;
- exposing the vial sensor system to a light source; and
- detecting fluorescent light emitted from the vial sensor system to create fluorescent light data, wherein the fluorescent light data is indicative of biological activity.

* * * * *